United States Patent

Choh et al.

[11] Patent Number: 5,993,416
[45] Date of Patent: Nov. 30, 1999

[54] METHOD AND APPARATUS FOR REGULATING THE FLUID FLOW RATE TO AND PREVENTING OVER-PRESSURIZATION OF A BALLOON CATHETER

[75] Inventors: Richard T. Choh, Waltham; John R. Fagan, Pepperell; Stephen J. Forcucci, Arlington, all of Mass.

[73] Assignee: Medtronic AVE, Inc., Santa Rosa, Calif.

[21] Appl. No.: 09/007,427

[22] Filed: Jan. 15, 1998

[51] Int. Cl.$^6$ .................................................. A61M 29/00
[52] U.S. Cl. ................................................. 604/99; 604/49
[58] Field of Search ................................. 604/99, 96, 97, 604/49, 101, 100, 118; 606/192–194

[56] References Cited

U.S. PATENT DOCUMENTS

| | | |
|---|---|---|
| 2,245,271 | 6/1941 | Guill . |
| 4,062,360 | 12/1977 | Bentley . |
| 4,143,853 | 3/1979 | Abramson . |
| 4,449,693 | 5/1984 | Gereg . |
| 4,703,759 | 11/1987 | Merrick et al. . |
| 4,931,050 | 6/1990 | Idriss . |
| 5,061,253 | 10/1991 | Yoshida . |
| 5,084,021 | 1/1992 | Baldwin . |
| 5,098,405 | 3/1992 | Peterson et al. . |
| 5,221,268 | 6/1993 | Barton et al. . |
| 5,238,026 | 8/1993 | Goto . |
| 5,273,542 | 12/1993 | Blake, III . |
| 5,300,034 | 4/1994 | Behnke et al. . |
| 5,318,515 | 6/1994 | Wilk . |
| 5,336,174 | 8/1994 | Daoud et al. . |
| 5,336,192 | 8/1994 | Palestrant . |
| 5,409,477 | 4/1995 | Caron et al. . |
| 5,453,096 | 9/1995 | Lataix . |
| 5,453,097 | 9/1995 | Paradis . |
| 5,499,968 | 3/1996 | Milijasevic et al. . |
| 5,505,701 | 4/1996 | Lomana ..................................... 604/99 |
| 5,514,110 | 5/1996 | Teh . |
| 5,520,661 | 5/1996 | Lal et al. . |
| 5,520,665 | 5/1996 | Fleetwood . |
| 5,531,688 | 7/1996 | Hiejima et al. . |
| 5,752,935 | 5/1998 | Robinson et al. ..................... 604/99 X |
| 5,785,685 | 7/1998 | Kugler et al. .......................... 604/99 X |

FOREIGN PATENT DOCUMENTS 0399 119   11/1990   European Pat. Off. .

Primary Examiner—John D. Yasko
Attorney, Agent, or Firm—Richard L. Klein; Catherine C. Maresh

[57] ABSTRACT

The invention relates to an apparatus and method for limiting the pressure of inflation fluid injected into a drug delivery catheter balloon, while permitting continuous and uninterrupted flow of such fluid to the balloon. The apparatus includes an elongated hollow housing having a fluid entrance, a fluid exit and a bore extending therebetween which forms an interconnecting chamber and passageway. A piston and piston shaft assembly is disposed inside the housing and is longitudinally movable within the chamber. The piston and piston shaft assembly is biased against the fluid pressure of the fluid entering the housing by a spring. The piston shaft has a distal end which extends toward the passageway inlet. As the incoming fluid pressure increases and approaches the predetermined maximum pressure level of the apparatus, the piston shaft distal end moves within the chamber against the biasing force of the spring toward a position adjacent the passageway inlet. When the incoming fluid pressure reaches and exceeds the predetermined maximum pressure level, the piston shaft distal end enters and extends into the passageway, thereby forming an annulus within the passageway. The annulus functions to restrict the flow rate and limit the pressure of the fluid exiting the housing and entering the catheter balloon.

17 Claims, 3 Drawing Sheets

METHOD AND APPARATUS FOR REGULATING THE FLUID FLOW RATE TO AND PREVENTING OVER-PRESSURIZATION OF A BALLOON CATHETER

FIELD OF INVENTION

The present invention relates to catheter techniques and devices for delivering therapeutic and/or diagnostic agents to a site within a patient's vasculature or bodily organ. More particularly, the present invention relates to a method and apparatus for regulating the flow rate of a fluid agent to and preventing the over-pressurization of a perforated drug delivery balloon catheter.

BACKGROUND OF THE INVENTION

Various drug delivery catheter designs and procedures have been developed over the last several years for use in a wide range of medical applications. One such design and procedure involves the delivery of therapeutic and/or diagnostic agents to a localized area of a patient's vasculature through the use of a perforated balloon catheter. Typically, such prior art drug delivery catheters include a balloon having a plurality of apertures spaced about its surface located at the distal end of the catheter. The interior of the balloon is in fluid communication with an inflation lumen which extends throughout the length of the catheter. After the balloon has been placed within the patient's vasculature or other bodily organ at the position of the treatment site, inflation fluid comprising a therapeutic or diagnostic agent is injected under pressure through the inflation lumen and into the balloon. The pressurized inflation fluid fills the balloon, migrates through the apertures in the balloon wall and penetrates the tissue wall at the treatment site. The balloon apertures are sized such that the balloon remains pressure-inflated despite the flow of the fluid agent through the apertures in the balloon wall.

Perforated balloon drug delivery catheters such as the one described above are capable of delivering a wide range of therapeutic and/or diagnostic agents. For example, perforated balloon catheters are designed for use in conjunction with angioplasty dilatation for treating the site of an opened atherosclerotic lesion or stenosis with a therapeutic agent such as heparin to inhibit unregulated smooth muscle cell proliferation and prevent restenosis. Alternatively, perforated balloon catheters may be used to deliver a drug or agent to dissolve a stenosis in an effort to avoid use of angioplasty or atherectomy procedures, or to deliver a thrombolytic agent to dissolve a clot at the lesion site. In addition, perforated balloon catheters also may be used to administer antibiotics or anesthetics directly to the treatment site prior to removal of the catheter. Other agents which may be administered through perforated balloon catheters include steroids for suppressing inflammation in a localized tissue site, anti-neoplastic for treating a tumor site, chemotherapeutics or any desired mixture of individual pharmaceuticals.

Despite the development of this broad range of applications for perforated balloon drug delivery catheters, improvement in the control of the infusion of the inflation fluid to the treatment site is desirable. Typically, the inflation fluid is manually injected into the perforated drug delivery balloon catheter by means of a syringe device comprising a syringe plunger and barrel. Accordingly, the rate of infusion of the inflation fluid to the treatment site depends on the pressure applied on the syringe plunger by the physician when expelling the inflation fluid from the syringe device. It has been found that the precise control of the pressure at which the inflation fluid is injected into the catheter is important, thus requiring great skill on the part of the administering physician. For example, the exertion of excessive pressure on the syringe plunger by the physician may result in over-pressurization of the inflation fluid within the balloon, such over-pressurization may cause high velocity jetting of the inflation fluid through the balloon apertures and possible trauma to the interior walls of the patient's vasculature.

Moreover, it has been found that the use of a pressure gauge to assist the physician in monitoring the pressure at which the inflation fluid is injected into the catheter does not assure precise control of the infusion of inflation fluid to the treatment site. For example, a drop in the pressure indicated on the pressure gauge generally causes the physician to accelerate the movement of the syringe plunger into the syringe barrel, thereby resulting in a pressure spike. Any such pressure spike may result in over-pressurization of the balloon and, consequently, possible high velocity jetting of inflation fluid through the balloon apertures.

In an effort to prevent high velocity jetting resulting from over-pressurization of the fluid within the perforated balloon, various forms of shut-off valves have been developed for limiting the pressure of the inflation fluid within the balloon. However, because these valves are designed to remain closed when the inflation fluid pressure exceeds a predetermined maximum allowable pressure, the flow of inflation fluid through the catheter to the treatment site may be discontinued for an indefinite period of time. It is understood that leaving the catheter in the patient's vasculature for any such prolonged period of time can adversely effect the patient's blood flow and thereby complicate the procedure. Moreover, the efficacy of the procedure may be compromised by a prolonged and an interrupted application of the drug to the treatment site.

Therefore, there exists a need for a method and apparatus for limiting the pressure of the inflation fluid within the perforated balloon so as to prevent high velocity jetting of the fluid through the balloon wall, and also permitting the continuous and uninterrupted flow of the drug to the treatment site.

OBJECTS AND SUMMARY OF THE INVENTION

In accordance with the present invention, an apparatus and method are provided for limiting the pressure of inflation fluid injected into a perforated drug delivery catheter balloon while permitting a continuous and uninterrupted flow of such inflation fluid to the balloon. The invention relates to an apparatus and method for creating an annulus within the flow path between the pressurized source of inflation fluid and the catheter balloon when the pressure of the inflation fluid exceeds the predetermined maximum pressure level of the apparatus. The annulus functions to restrict the flow rate and limit the pressure of the inflation fluid which flows to the catheter balloon.

Generally, the apparatus of the present invention comprises an elongated hollow housing which is coupled in flow communication between the pressurized source of inflation fluid and the catheter balloon. The interior of the housing forms an interconnecting chamber and passageway. The chamber is designed to receive a piston and piston shaft assembly which is biased longitudinally within the chamber under the opposing forces exerted by the pressurized inflation fluid and a spring disposed within the chamber. The piston shaft includes a distal end which extends toward the passageway inlet. As the pressure of the inflation fluid increases and approaches the predetermined maximum pressure level of the present device, the piston shaft distal end moves toward the passageway inlet. When the pressure of the inflation fluid exceeds the predetermined maximum pressure level of the device, the piston shaft distal end enters and extends into the passageway and thereby creates an annulus within the passageway. The annulus has the effect of restricting the flow rate and limiting the pressure of inflation fluid passing through the device and into the balloon. A further aspect of the invention includes means for adjusting the maximum pressure level of the apparatus.

It is, therefore, a principal object of the present invention to provide a method and apparatus for use with a perforated drug delivery balloon catheter to prevent the over-pressurization of the balloon and provide the continuous and uninterrupted flow of the drug agent to the treatment site.

It is a further object of the present invention to provide an apparatus for use in a drug delivery balloon catheter which may be adjusted for localized delivery of therapeutic and/or diagnostic agents having different fluid characteristics.

It is also an object of the present invention to provide an apparatus for use in a drug delivery balloon catheter to enable efficient drug delivery and to prevent the waste of excess portions of such drug injected into the catheter.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

DESCRIPTION OF THE PREFERRED EMBODIMENTS

Referring generally to the embodiments of the invention shown in the accompanying drawings, wherein like reference numbers refer to like parts throughout the various views, the basic principles of the broadest aspects of the invention can be appreciated from FIGS. 1–4.

Figure 1:
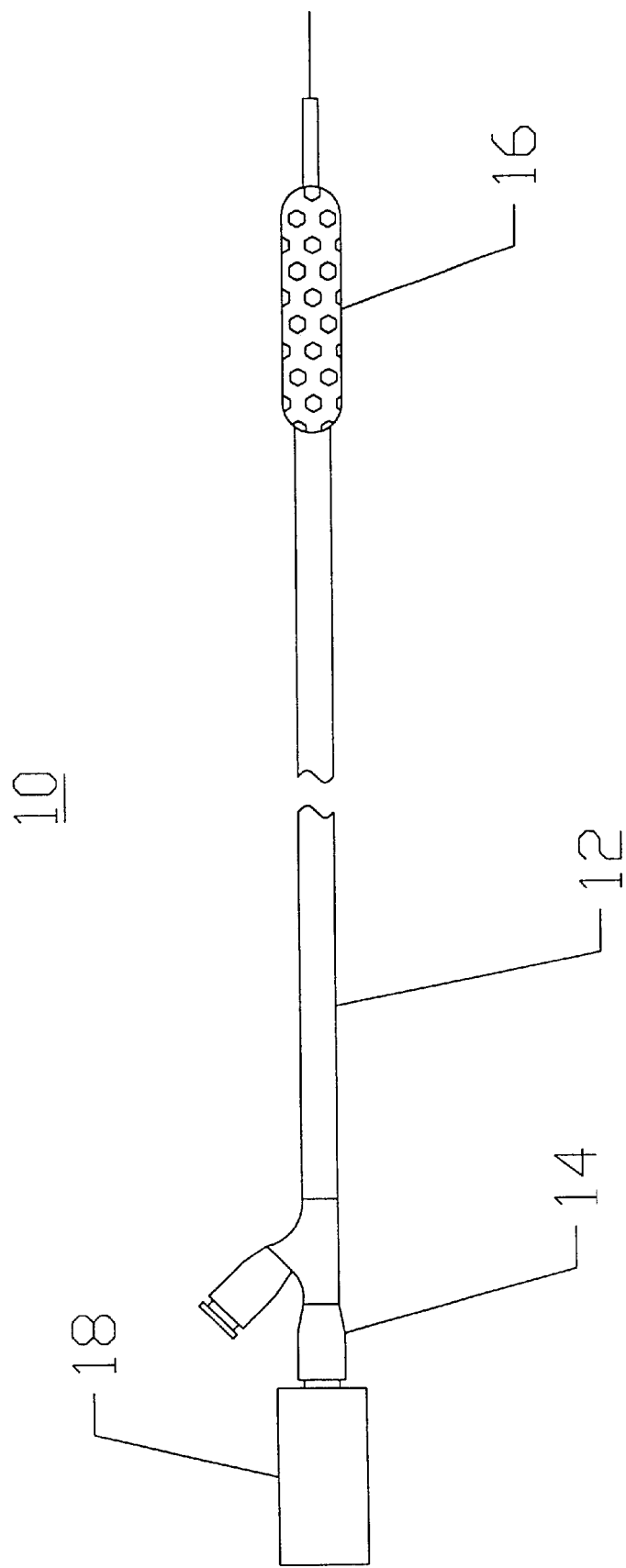
FIG. 1 is a schematic drawing showing a plan view of a balloon catheter employing the over-inflation protection apparatus according to the present invention.

As shown in FIG. 1, a drug delivery balloon catheter 10 generally comprises a catheter tube 12 having a perforated balloon 16 located at its distal end. Catheter tube 12 further includes at least one inflation lumen which extends longitudinally throughout essentially the entire length of the catheter tube and provides flow communication between the interior of the balloon 16 and a syringe or other pressure infusion device coupled to an injection port 14 located at the proximal end of catheter tube 12.

In accordance with one embodiment of the present invention, the device 18 is coupled in flow communication between injection port 14 and the source of pressurized inflation fluid (not shown). In this arrangement, the fluid agent is introduced into the device 18 under pressure via a syringe prior to entering injection port 14 and traveling through the inflation lumen to balloon 16.

Figure 2:
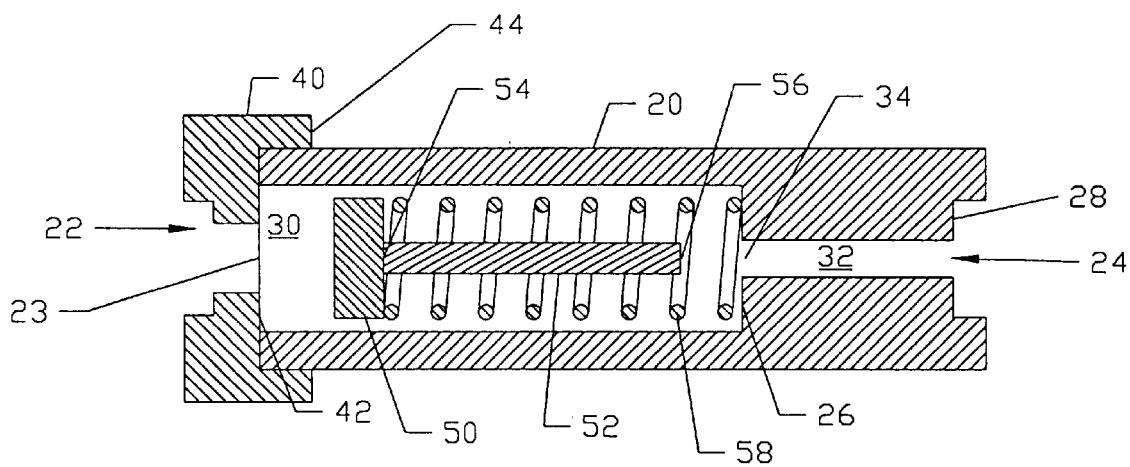
FIG. 2 is a longitudinal cross-sectional view of an embodiment of a basic form of the present invention wherein the piston and piston shaft are in open positions.

The present invention, as illustrated in a basic form in FIG. 2, provides means for controlling the flow rate of the fluid agent and regulating the pressurization of the balloon during a catheterization procedure. As here embodied, the device of the present invention comprises an elongated hollow body having a cap 40 and housing 20. Housing 20 includes a bore extending throughout its length defining an inlet 23 at one end and a manifold outlet 24 at the opposite end, wherein the bore consists of two interconnecting sections having different diameters. A first section defining a chamber 30 extends from inlet 23 to annular shoulder 26. A second section having a smaller diameter than the first section and defining a passageway 32 extends from annular shoulder 26 to annular shoulder 28 formed at manifold outlet 24. Passageway 32 includes an inlet 34 in flow communication with chamber 30.

Cap 40 comprises a hollow tube which forms an inlet manifold 22 adapted to receive pressurized fluid from a syringe, or any other pressurized source acceptable for use with a catheter device. As shown in FIG. 2, cap 40 is removably coupled to housing 20, such that manifold inlet 22 is in flow communication with chamber 30 within housing 20. Cap 40 may be coupled to housing 20 by any of several different means known in the art. For example, the inside surface of cap 40 between annular shoulder 42 and outlet end 44 may be fitted with a screw thread which mates with a complementary screw thread fitted on the outside surface of housing 20 adjacent inlet 23. Alternatively, it will also be understood that the hollow elongated body formed by housing 20 and cap 40 may be manufactured as a single unit.

As further shown in FIG. 2, piston 50 is slidably received within chamber 30, such that its front surface faces inlet 23 and its back surface faces passageway inlet 34. Piston 50 is coupled at its back surface to the proximal end 54 of piston shaft 52. Piston shaft 52 is disposed longitudinally within chamber 30, having a distal end 56 extending toward passageway inlet 34. The diameter of piston shaft 52 is dimensioned to be smaller than the diameter of passageway 32 such that when piston shaft distal end 56 extends through inlet 34 and into passageway 32 an annulus is formed which restricts the flow rate and pressure of fluid passing from chamber 30, into passageway 32 and through manifold outlet 24.

With reference to FIG. 2, piston 50 and piston shaft 52 are normally maintained in an open position by the biasing force of helical compression spring 58, which encircles piston shaft 52 and is interposed between the back surface of piston 50 and annular shoulder 26. As will be understood with reference to the operation of the present invention as described below, the length and/or compression constant of spring 58, or the length of piston shaft 52 may be varied to provide a specific predetermined maximum allowable pressure value for the device. It will be understood that alternative devices for biasing piston 50 in a normally open position such as a compressible resilient membrane may be substituted for spring 58.

Housing 20 is designed to permit the passage of fluid from manifold inlet 22, through chamber 30 and passageway 32, and to manifold outlet 24. To this end, piston 50 is disposed within chamber 30 such that fluid may readily pass between the outer side surface of piston 50 and the inner wall of housing 20 which forms chamber 30. Alternatively, other means may be included for providing flow communication between manifold inlet 22 and passageway inlet 34. For example, the outer periphery of piston 50 may include one or more ducts extending from the piston front surface to its back surface.

In operation, the device 18 is initially coupled at manifold inlet 22 to a syringe containing pressurized fluid agent and at manifold outlet 24 to the injection port of a balloon catheter as shown in FIG. 1. Referring now to FIG. 2, prior to the introduction of the fluid agent, piston 50 and distal end 56 of piston shaft 52 are maintained in their normally-open positions under the biasing force exerted by spring 58. When the device is in this state, there is provided a continuous flow path for the fluid agent to pass from manifold inlet 22, through chamber 30 and passageway 32, and out manifold outlet 24.

After the balloon has been positioned across the treatment site within the patient's vasculature or other bodily organ, the fluid agent is injected under pressure into manifold inlet 22. The fluid agent then travels through chamber 30 and passageway 32, before entering the proximal end of the catheter lumen coupled to manifold outlet 24. The fluid agent continues through the catheter lumen and into balloon 16 where it migrates through the apertures in the balloon wall to the treatment site. While passing through chamber 30 the inflation fluid exerts a force on the front surface of piston 50 urging the piston and connected piston shaft 52 toward passageway inlet 34. It is understood that the force exerted on piston 50 by the fluid agent is directly proportionate to the pressure under which the fluid agent is injected into manifold inlet 22. To this end, as the pressure of the inflation fluid within chamber 30 increases, piston 50 and piston shaft 52 will move longitudinally within chamber 30 toward the passageway inlet 34 until the force exerted by the fluid agent on piston 50 is in equilibrium with the counteracting force of compression spring 58.

Figure 3:
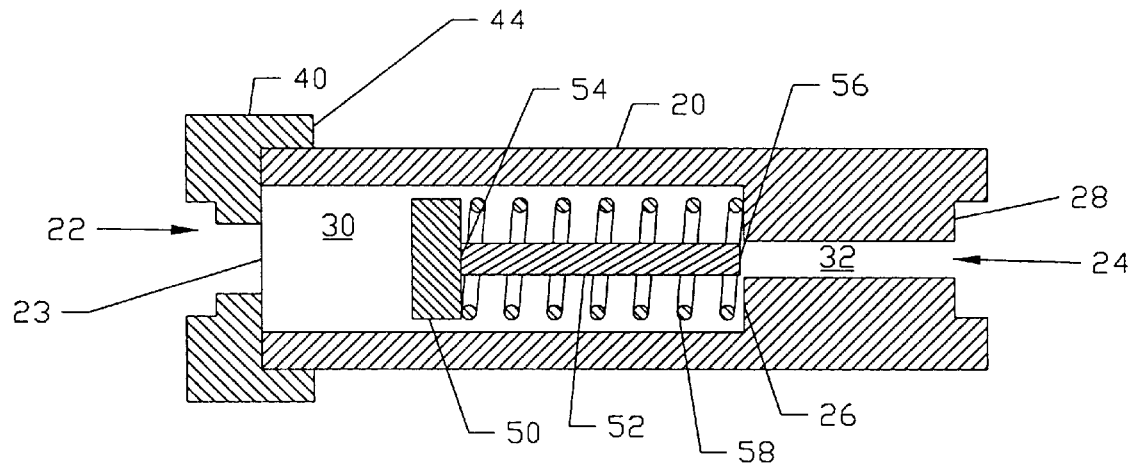
FIG. 3 is a longitudinal cross-sectional view of the embodiment of the present invention shown in FIG. 2 wherein the piston shaft distal end is approaching a flow regulating position.

Referring now to FIG. 3, as the pressure of fluid agent within chamber 30 approaches the predetermined maximum allowable pressure level of the present invention, piston shaft distal end 56 will advance to a position immediately adjacent to passageway inlet 34. Furthermore, as demonstrated in FIG. 4 when the pressure exerted by the fluid agent on piston 50 reaches and/or exceeds the predetermined maximum pressure level, piston shaft distal end 56 enters passageway inlet 34, thereby creating an annulus within passageway 32 which limits the area through which the inflation fluid may flow through passageway 32. The annulus formed within passageway 32 functions to restrict the flow rate of fluid through passageway 32 and to create a pressure drop across the length of the annulus. Should the pressure of the fluid agent further increase beyond the predetermined maximum pressure value, piston shaft distal end 56 will extend further into passageway 32 and increase the length of the annulus. It will be understood that the amount of the pressure drop across the annulus is directly proportionate to the length of the annulus formed by piston shaft 52 within passageway 32. Thus, the greater the length of the annulus formed within passageway 32, the greater the amount of the pressure drop across the annulus. Moreover, the relative dimensions of piston shaft 52 and passageway 32 are designed such that the amount of the pressure drop across the annulus is equal to the amount to which the pressure of the fluid within chamber 30 exceeds the predetermined maximum pressure level of the device. Thus ensuring that the pressure of the inflation fluid passing through passageway 32 and into balloon 16 will never exceed the predetermined maximum allowable pressure for the device of the present invention.

Preferably, the present invention may be adapted to provide different maximum allowable pressures for the fluid agent passing through the device and into the catheter balloon. To this end, in a preferred form of the present invention the normally-open position of the piston shaft distal end 56 may be adjusted relative to passageway inlet 34. It will be understood that by positioning the piston shaft distal end 56 either closer or further from passageway inlet 34 one can vary the amount of fluid pressure required to force piston shaft distal end 56 into passageway 32.

Figures 5, 6, 7:
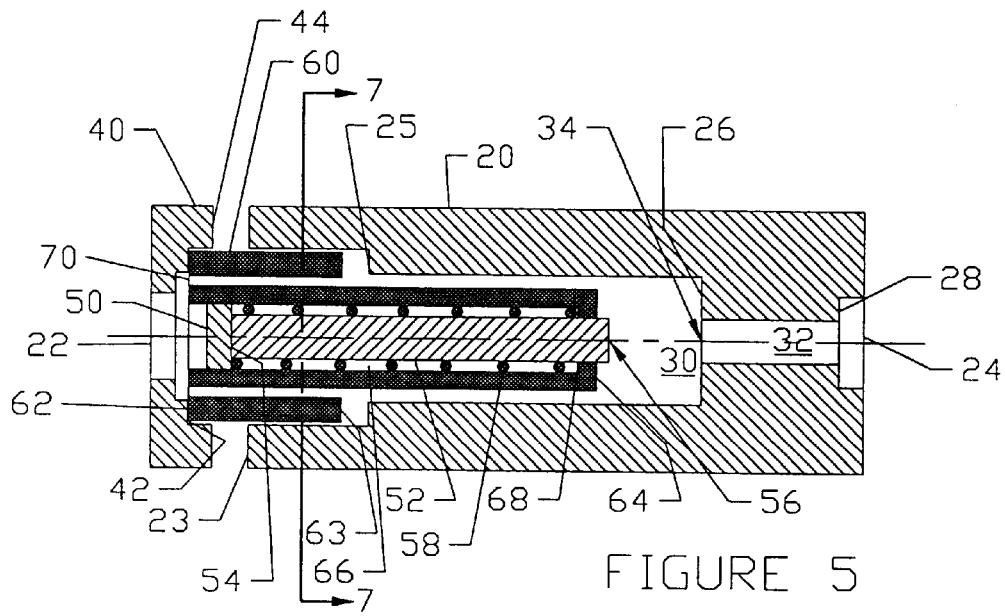
FIG. 5 is a longitudinal cross-sectional view of a preferred embodiment of the present invention which provides for varying the predetermined maximum pressure level of the device.
FIG. 6 is a longitudinal cross-sectional view of the preferred embodiment shown in FIG. 5 wherein the longitudinal position of the piston shaft distal end has been adjusted relative to the passageway inlet.
FIG. 7 is a sectional view taken along line 7—7 of FIG. 5.

One embodiment of this preferred form of the invention, as illustrated in FIG. 5, comprises an outer housing 20, inner housing 60 and cap 40. Outer housing 20 includes a bore extending longitudinally throughout its length, forming an inlet 23 and a manifold outlet 24. The bore in the outer housing 20 consists of three interconnecting sections having different diameters. A first section and a second section define a chamber 30 extending from inlet 23 to annular shoulder 26. The first section extends from inlet 23 to annular shoulder 25. The second section has a smaller diameter than the first section and extends from annular shoulder 25 to annular shoulder 26. The third section has a smaller diameter than the second section and defines a passageway 32 extending from annular shoulder 26 to annular shoulder 28 formed at manifold outlet 24. Passageway 32 includes an inlet 34 in flow communication with chamber 30.

As further illustrated in FIG. 5, inner housing 60 is longitudinally disposed within chamber 30 of outer housing 20. Inner housing 60 includes a first section adjacent inlet end 62 and a second section adjacent outlet end 64, having outside diameters which generally correspond to the diameters of the first and second sections of chamber 30, respectively. The first section of inner housing 60 extends from inlet end 62 to annular shoulder 63. Whereas, the second section extends from annular shoulder 63 to outlet end 64.

According to this embodiment, inner housing 60 is adjustably coupled within outer housing 20 such that the longitudinal position of piston shaft distal end 56 relative to passageway inlet 34 may be varied. To this end, the outside surface of the first section of inner housing 60 is fitted with a screw thread which mates with a complementary screw thread fitted on the inside surface of the portion of outer housing 20 that defines the first section of chamber 30. Thus, by rotating the outer housing relative to the inner housing the longitudinal position of inner housing 60 may be adjustably disposed within outer housing 20 to vary the distance between piston shaft distal end 56 and passageway inlet 34 when piston 50 and piston shaft 52 are in the normally open position. FIGS. 5 and 6 illustrate the adjustable feature of the preferred embodiment showing two different longitudinal positions for piston shaft distal end 56 relative to passageway inlet 34 when the device is in a normally open position.

As described with reference to FIGS. 5 and 7, inner housing 60 includes a concentric cylindrical bore 66 extending throughout its length and having openings at the inlet end 62 and outlet end 64. In addition, the outside perimeter of the inner housing wall includes one or more ducts 70, extending from inlet end 62 to annular shoulder 63.

Referring now to FIG. 5, piston 50 is received into bore 66. Piston 50 is coupled to the proximal end 54 of piston shaft 52. Piston shaft 52 is disposed longitudinally within bore 66, having a distal end 56 extending through an opening in outlet end 64. Piston 50 is normally maintained in a fully open position by the biasing force of helical compression spring 58, which encircles piston shaft 52 and is interposed between the back surface of piston 50 and shoulder 68 formed at the outlet end of bore 66.

Cap 40 comprises a hollow tube which forms an inlet manifold 22 adapted to receive pressurized fluid from a syringe, or any other pressurized source acceptable for use with a catheter device. As shown in FIG. 5, cap 40 is removably coupled to inner housing 60, such that the inlet manifold 22 is in flow communication with the inlet end of bore 66 and ducts 70. Cap 40 may be coupled to inner housing 60 by any of several different means known in the art. For example, the inside surface of cap 40 between annular shoulder 42 and outlet end 44 may be fitted with a complementary screw thread fitted which mates with the screw thread on the outside surface of the first section of the inner housing.

When the pressure of the inflation fluid is at or below the maximum allowable pressure selected, this embodiment of the present invention is designed to permit the flow of pressurized inflation fluid from manifold inlet 22 to manifold outlet 24. To this end, the diameter of the second section of chamber 30 is dimensioned to be slightly larger than the diameter of second section of inner housing 60. Accordingly, when the inner housing 60 is engaged with the outer housing 20 and cap 40, the inflation fluid is designed to pass from manifold inlet 22, through ducts 70, into the space within chamber 30 between the outside surface of inner housing 60 and the inside surface of outer housing 20 before entering passageway 32.

Likewise, if the pressure of the inflation fluid entering manifold inlet 22 exceeds the maximum allowable pressure, the invention is designed to simultaneously restrict the flow and limit the pressure of inflation fluid traveling through passageway 32 and into the catheter. To this end, passageway 32 is dimensioned to have a cross-sectional diameter slightly larger than the cross-sectional diameter of piston shaft 52, such that an annulus is formed when the distal end 56 of piston shaft 52 extends into passageway 32.

Figure 4:
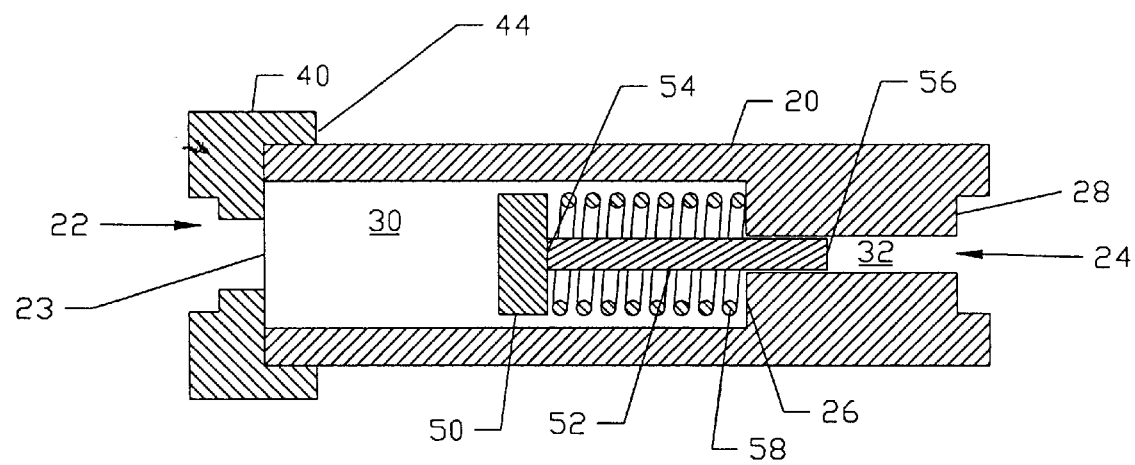
FIG. 4 is a longitudinal cross-sectional view of the embodiment of the present invention shown in FIG. 2 wherein the piston shaft distal end is in a flow regulating position.

In operation, the preferred embodiment shown in FIGS. 5 and 7 functions in generally the same manner as described above with respect to the basic embodiment shown in FIGS. 2–4. However, prior to the injection of inflation fluid the preferred embodiment of FIGS. 5 and 7 may be adjusted to vary the maximum allowable pressure of inflation fluid which may pass through the device and into the catheter balloon.

While only a few embodiments have been illustrated and described in connection with the present invention, various modifications and changes in the apparatus will become apparent to those skilled in the art. All such modifications or changes falling within the scope of the claims are intended to be included therein.

We claim:

1. An apparatus for limiting the pressure and regulating the flow of inflation fluid entering a catheter balloon, comprising:

(a) a housing having an inlet port, an outlet port and a bore extending longitudinally throughout providing flow communication between the inlet port and the outlet port, wherein the bore forms a chamber adjacent the inlet port having a diameter and a passageway adjacent the outlet port having a smaller diameter than the chamber diameter;

(b) a piston longitudinally movable within the chamber having a front surface in flow communication with the inlet port;

(c) biasing means disposed within the chamber for biasing the piston against the force exerted by pressurized fluid entering the inlet port, such that as the pressure of the fluid passing through the inlet port and into the chamber variably increases to a predetermined maximum pressure level, the piston moves within the chamber in a direction opposite the biasing force;

(d) a piston shaft having a proximal end coupled to a back surface of the piston and a distal end extending toward the passageway inlet, such that when the pressure of the fluid entering the inlet port exceeds a predetermined maximum pressure level the piston shaft distal end enters the passageway inlet and creates an annulus within the passageway.

2. The apparatus according to claim 1, wherein the longitudinal position of the piston shaft distal end may be adjusted within the chamber relative to the passageway inlet when the piston shaft is in a normally-open position.

3. The apparatus according to claim 1, wherein the biasing means comprises a spring.

4. The apparatus according to claim 1, wherein the housing comprises a body portion and a removable cap.

5. A apparatus for limiting the pressure and regulating the flow of inflation fluid entering a catheter balloon, comprising:

(a) an outer housing having an inlet port, an outlet port and a bore extending longitudinally throughout providing flow communication between the inlet port and the outlet port, wherein the bore forms a chamber adjacent the inlet port having a diameter and a passageway adjacent the outlet port having a smaller diameter than the chamber diameter;

(b) an inner housing disposed within the outer housing having a bore extending longitudinally throughout forming a hollow cylinder with an inlet in flow communication with the outer housing inlet port and an outlet in flow communication with the outer housing chamber;

(c) means for providing flow communication for inflation fluid between the outer housing inlet port and the passageway inlet;

(d) a piston longitudinally movable within the cylinder having a front surface in flow communication with the outer housing inlet port;

(e) biasing means disposed within the hollow cylinder for biasing the piston against the force exerted by the pressurized fluid entering the inner housing inlet, such that as the pressure of the fluid passing through the outer housing inlet port and into the inner housing inlet variable increases to a predetermined level, the piston moves within the hollow cylinder in a direction opposite the force exerted by the biasing means;

(f) a piston shaft having a proximal end coupled to a back surface of the piston and a distal end extending through the cylinder and toward the passageway inlet, such that when the pressure of the fluid entering the inlet port exceeds a predetermined maximum pressure level the piston shaft distal end enters the passageway inlet and creates an annulus within the passageway.

6. The apparatus according to claim 5, wherein the longitudinal position of the inner housing relative to the outer housing may be adjusted such that the distance between the piston shaft distal end and the passageway inlet may be varied when the piston shaft is in a normally-open position.

7. The apparatus according to claim 5, wherein the biasing means comprises a spring.

8. The apparatus according to claim 5, wherein the means for providing flow communication of inflation fluid between the outer housing inlet port and the passageway inlet comprises a plurality of ducts extending longitudinally throughout the length of the inner housing wall.

9. The apparatus according to claim 5, wherein the outer housing comprises a body portion and a removable cap.

10. An apparatus for limiting the pressure and regulating the flow of inflation fluid entering a catheter balloon, comprising:

(a) an outer housing having a inlet end, an outlet port and a bore extending longitudinally throughout providing flow communication between the inlet end and the outlet port, wherein the bore forms a chamber adjacent the outer housing inlet end having a diameter and a passageway adjacent the outlet port having a diameter smaller than the chamber diameter;

(b) an inner housing disposed within the outer housing chamber, having a bore extending longitudinally throughout forming a hollow cylinder with an inlet and an outlet in flow communication with the passageway inlet;

(c) a cap having an inlet port, an outlet end and a bore extending longitudinally throughout providing flow communication between the inlet port and the outlet end, wherein the cap outlet end is coupled to the inlet end of the inner housing such that the inlet port is in flow communication with the inner housing inlet;

(d) means for providing flow communication for inflation fluid between the inlet port and the passageway inlet;

(e) a piston longitudinally movable within the inner housing hollow cylinder and having a front surface in flow communication with the inlet port;

(f) biasing means disposed within the hollow cylinder for biasing the piston against the pressure of the fluid entering from the inlet end of the inner housing hollow cylinder, such that as the pressure of the fluid passing through the inlet port and into the inner housing inlet variably increases to a predetermined level, the piston moves within the inner housing cylinder in a direction opposite the force exerted by the biasing means; and (g) a piston shaft coupled at a proximal end to a back surface of the piston and having a distal end extending through the inner housing hollow cylinder and into the outer housing chamber, such that when the pressure of the fluid entering the inlet port exceeds a predetermined maximum pressure level the piston shaft distal end enters the passageway inlet and creates an annulus within the passageway.

11. The apparatus according to claim 10, wherein the inner housing is adjustably coupled to the outer housing such that the longitudinal position of the piston shaft distal end relative to the passageway inlet may be varied.

12. The apparatus according to claim 10, wherein the biasing means is a spring.

13. The apparatus according to claim 10, wherein the means for providing flow communication of inflation fluid between the outer housing inlet port and the passageway inlet comprises a plurality of ducts extending longitudinally throughout the length of the inner housing wall.

14. A method for limiting the pressure and providing an uninterrupted flow of fluid passing from a source of pressurized fluid to a catheter balloon, comprising:

(a) providing a passageway in flow communication between the source of pressurized fluid and the catheter balloon;

(b) passing fluid from the source of pressurized fluid through the passageway and into the balloon; and (c) forming an annulus within the passageway which restricts the flow rate of fluid passing through the passageway and creates a pressure drop across the length of the annulus when the pressure of the fluid entering the passageway exceeds a predetermined maximum pressure level.

15. The method according to claim 14, wherein the annulus within the passageway is formed by disposing a shaft within the passageway, wherein the shaft has a smaller cross-sectional area than the passageway.

16. The method according to claim 15, wherein the predetermined maximum pressure level may be varied.

17. The method according to claim 15, wherein the pressure drop across the length of the annulus is equal to the difference between the pressure of the fluid entering the passageway and the predetermined maximum pressure level.

* * * * *